United States Patent [19]

Denis et al.

[11] Patent Number: 4,956,496

[45] Date of Patent: Sep. 11, 1990

[54] PROCESS FOR ALLYLATION OF PERHALOALKYL-, PERHALOALKOXY- AND PERHALOALKYLTHIOANILINES IN THE PRESENCE OF A CATALYST

[75] Inventors: Jean-Pierre Denis, Doyet; Jean-Roger Desmurs, Communay; Jean-Pierre LeCouve, Caluire, all of France

[73] Assignee: Rhone-Poulenc Chimie, Courbevoie Cedex, France

[21] Appl. No.: 288,880

[22] Filed: Dec. 23, 1988

[30] Foreign Application Priority Data

Dec. 23, 1987 [FR] France ............................ 87 18011

[51] Int. Cl.$^5$ ........................................... C07C 209/10
[52] U.S. Cl. .................................................. 564/404
[58] Field of Search .................... 564/404, 440, 442

[56] References Cited

U.S. PATENT DOCUMENTS

| | | | |
|---|---|---|---|
| 2,286,678 | 6/1942 | Gubelmann | 260/574 |
| 3,642,902 | 2/1972 | Bach et al. | 260/585 R |
| 3,668,254 | 6/1972 | D'Amico et al. | 260/576 |
| 4,701,560 | 10/1987 | Regimbean et al. | 564/404 |

FOREIGN PATENT DOCUMENTS 0169449 9/1985 Japan .

OTHER PUBLICATIONS

Aresta et al., "Journal of Chemical Society Dalton", 1977, pp. 493–496.
Aresta et al., "Synth. React. Inorg. Net. Org. Chem.", vol. 9, No. 2, 1979, pp. 157–175.

Primary Examiner—Richard L. Raymond
Assistant Examiner—Peter G. O'Sullivan
Attorney, Agent, or Firm—Finnegan, Henderson, Farabow, Garrett and Dunner

[57] ABSTRACT

A process for the allylation of perhaloalkyl-, perhaloalkoxy- and perhaloalkylthioanilines. A perhaloalkylated-, perhaloalkoxylated- and perhalothioalkylated aniline and an allyl halide in a solvent medium are placed in contact with an effective amount of a metal selected from palladium, copper and nickel.

16 Claims, No Drawings

PROCESS FOR ALLYLATION OF PERHALOALKYL-, PERHALOALKOXY- AND PERHALOALKYLTHIOANILINES IN THE PRESENCE OF A CATALYST

The present invention relates to a process for the preparation of N-allyl perhaloalkyl-, perhaloalkoxy- and perhaloalkylthioanilines. It relates more particularly to a process for allylation of meta-trifluoromethylaniline in the presence of metals.

It is known, for example from U.S. Pat. No. 2,286,678 to condense allyl bromide with an aminophenol in the presence of potassium carbonate in an alcoholic solvent. The allylation yield is in the region of 50%, which is quite important considering the high cost of the raw materials.

It is also known, from U.S. Pat. No. 3,668,254, to prepare N-haloallyl-p-phenylenediamines by condensation of 2,3-dichloropropene with 4-aminodiphenylamine in the presence of stoichiometric quantities of triethylamine and in the absence of a solvent. The yield by the process disclosed at column 2, lines 20–35 of U.S. Pat. No. 3,668,254 (see col. 2, lines 20–35) was very low at approximately 38%. The method described in this patent could not, therefore, be adapted to raw materials as costly as meta-trifluoromethylaniline.

In the case of meta-trifluoromethylaniline, attempts have been made to obtain yields which are as high as possible. It should also be noted that meta-trifluoromethylaniline is a compound which is strongly deactivated chemically, and whose substitution is much more difficult than that of derivatives such as para-phenylenediamine, which is itself activated and therefore promotes substitutions.

The industry was confronted with the problem of obtaining an N-allylation of meta-trifluoromethylaniline in proper yields, which was much more difficult to substitute than the activated compounds described in the prior art.

The present invention solves this problem by providing a process for allylation of perhaloalkyl-, perhaloalkoxy- and perhaloalkylthioanilines which comprises placing perhaloalkylated, perhaloalkoxylated or perhalothioalkylated aniline and an allyl halide in a solvent medium in contact with an effective amount of a metal catalyst selected from palladium, copper and nickel.

Preferred perhaloalkyl-, perhaloalkoxy- or perhalothioalkylanilines are compounds represented by the following formula (I):

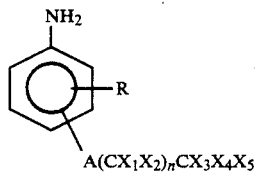

in which:

A is a covalent bond or an oxygen or sulfur atom, $X_1$, $X_2$, $X_3$, $X_4$ and $X_5$ each represent an identical or different halogen atom, n is equal to 0, 1 or 2, and R is a hydrogen atom, a halogen atom, an alkyl containing 1 to 4 carbon atoms, an alkoxy containing 1 to 4 carbon atoms or an aryl group.

All these anilines are compounds which are strongly deactivated and whose substitution is difficult.

It is also known according to U.S. Pat. No. 3,642,902 to perform the allylation of aniline (see Example V), a compound which is not deactivated, using bis(allylpalladium) chloride complexes. The allylation yield reported in Example V, the only example using aniline as the starting material, is only 23%.

It is also known according to the papers by Aresta, published in Synth. React. Inorg. Met. Org. Chem. 9(2), 157–174, 1979 and in the Journal of Chemical Society Dalton, (1977), 493, to prepare complexes of palladium II and N-allylanilines. These complexes easily decompose and release methylacetylene and a PD-aniline complex. In view of U.S. Pat. No. 3,642,902 and the papers by Aresta, it would have been impossible to envision an industrial process employing metals such as palladium. This is because of the risk of formation of the palladium-N-allylaniline complexes, which decompose and result in the loss of N-allylaniline.

Accordingly, it has been quite surprising to find that when placing a perhaloalkylated, perhaloalkoxylated or perhalothioalkylated aniline in contact with an allyl halide in the presence of a metal chosen from palladium, nickel and copper, there is no degradation of the resulting N-allylaniline, which can be produced in excellent yield based on the converted aniline.

As indicated above, the process of the present invention is catalyzed with an effective amount of a metal catalyst selected from palladium, copper and nickel. These metals may be in the form of metal salts having an oxidation state of I or II, which preferably include chloride, sulfate, acetate or oxide. Included among the salts, oxides and various complexes are palladium chloride, cuprous chloride, cupric chloride, nickel chloride, palladium sulfate, copper sulfate, nickel sulfate, cupric oxide, palladium acetate, cupric acetate, and palladium chloride complexed with benzonitrile.

The metal may also be present in the oxidation state of 0 and in metallic form such as copper powder, or in the form of a complex such as palladiumdiacetate or dibenzylideneacetonepalladium. Among the metals mentioned, the use of palladium is preferred.

The allyl halide is preferably chosen from allyl chloride and allyl bromide. Allyl chloride is most preferred.

The present invention may be carried out in polar aprotic solvents, ethers, nitriles, halogenated aromatic solvents, halogenated aliphatic solvents, or alcohols. Suitable aprotic solvents include N-methylpyrrolidone (NMP), N,N-dimethylformamide (DMF), N-methylformamide (NMF), or N,N-dimethylacetamide (DMA). Suitable ethers include tetrahydrofuran (THF), petroleum ether, or methyl tert-butyl ether. Suitable nitriles include benzonitrile or acetonitrile. Suitable halogenated aromatic solvents include toluene, xylene, chlorobenzene, or dichlorobenzene. Suitable halogenated aliphatic solvents, preferably containing 5 to 10 carbon atoms, include cyclohexane, or heptane. A suitable alcohol is ethanol. The use of polar aprotic solvents is preferred among these solvents.

Regarding the quantities of reactants employed, it is preferred to employ a molar ratio of allyl halide to aniline of from about 1:1 to 2:1 and a molar ratio of the catalyst to aniline of from about 0.01:1 and 0.5:1, more preferably from 0.05:1 to 0.2:1. The concentration of aniline in the solvent is preferably from about 100 g to 500 g per liter.

Regarding the reaction conditions, it is preferred to conduct the reaction at a temperature from about 50° to 120° C. for a period which can preferably range from about 2 to 24 hours.

The present invention will be described more completely with the aid of the following examples which should not in any event be considered as limiting it.

The meanings of the legends employed in the following examples are:

DC = the degree of conversion of the initial material $$DC = \frac{\text{number of moles of converted material}}{\text{number of moles of initial material}}$$

CY = the yield based on converted material $$CY = \frac{\text{number of moles of final product}}{\text{number of moles of converted material}}$$

EXAMPLES 1 TO 16

The following were introduced into a 30-ml reactor
0.65 g of m-trifluoromethylaniline (4 mmol),
0.61 g of allyl chloride (8 mmol),
2 ml of solvent, and
0.4 mmol of catalyst.

The mixture was agitated and heated to 75° C. for variable times. After cooling, 5 ml of 1N sodium hydroxide were added. The organic products were extracted with 5×5 ml of isopropyl ether. The organic phase was filtered through Clarcel ® silica and diluted to 25 ml in order to be determined by gas phase chromatography using internal standardization.

The degree of conversion of meta-trifluoromethylaniline and the yields based on converted N-allylaniline and N,N-diallylaniline are reported in the following Table I.

TABLE I

| Test | Catalyst | Solvent | Time | DC m-TFMA | CY N-allyl | CY N,N-diallyl |
| --- | --- | --- | --- | --- | --- | --- |
| Comparative 1 | without | CH$_3$CN | 2h 30 | 6.9 | 77.2 | traces |
| Invention 1 | PdCl$_2$ | CH$_3$CN | 2h 30 | 38.6 | 23.5 | |
| Invention 2 | CuCl$_2$ | CH$_3$CN | 2h 30 | 66.2 | 26.1 | 43 |
| Invention 3 | Pd(OAc)$_2$ | CH$_3$CN | 4h 30 | 78.7 | 38 | 26.2 |
| Invention 4 | PdCl$_2$(OCN)$_2$ | CH$_3$CN | 2h 30 | 23.7 | 69.6 | 2.5 |
| Invention 5 | Cu(OAc)$_2$ | CH$_3$CN | 2h 30 | 11.1 | 91.8 | 8.2 |
| Invention 6 | Cu$_2$O | CH$_3$CN | 2h 30 | 94.0 | 28 | 72 |
| Invention 7 | CuCl | CH$_3$CN | 3h 00 | 54.9 | 17.08 | 63.59 |
| Invention 8 | Cu° | CH$_3$CN | 3h 00 | 60.5 | 20.9 | 74.2 |
| Invention 9 | Cu$_2$O | CH$_3$CN | 3h 00 | 77.3 | 23.3 | 66.5 |
| Invention 10 | Pd(OAc)$_2$ | CH$_3$CN | 3h 00 | 39.9 | 35 | 2.5 |
| Invention 11 | 1% Pd(OAc)$_2$ | CH$_3$CN | 3h 00 | 12 | 55.8 | 0 |
| Comparative 2 | without | EtOH | 2h 30 | 29.6 | 93.5 | 5 |
| Invention 12 | Pd(DBA)$_2$ | EtOH | 2h 30 | 72.5 | 39.2 | 30.8 |
| Invention 13 | Pd(OAc)$_2$ | EtOH | 2h 30 | 57.8 | 43.3 | 14.2 |
| Invention 14 | NiSO$_4$ | EtOH | 2h 30 | 70.2 | 40.6 | |
| Comparative 3 | without | heptane | 2h 30 | 0 | 0 | 0 |
| Invention 15 | Pd(OAc)$_2$ | heptane | 2h 30 | 41.9 | 27 | 3.9 |
| Invention 16 | CuCl$_2$ | heptane | 2h 30 | 10.5 | 10 | traces |
| Comparative 4 | diallyl- palladium Cl complex | heptane | 12h 30 at 120° | 74 | 0 | 2 |

EXAMPLES 17 TO 18

The following were introduced into a 30-ml reactor
0.65 g of m-trifluoromethylaniline (4 mmol),
0.3 g of allyl chloride (4 mmol),
2 ml of solvent, and
0.4 mmol of catalyst.

The mixture was heated and agitated for 2 h 30 min. at 75° C. After cooling, 5 ml of 1N sodium hydroxide were added. The organic products were extracted with 5×5 ml of isopropyl ether. The organic phase was filtered through Clarcel ® silica and was diluted to 25 ml for determination using internal standardization.

The degree of conversion of trifluoromethylaniline and the yields based on converted N-allylaniline and N,N-diallylaniline are reported below in Table II.

TABLE II

| Test | Catalyst | Solvent | Time | DC m-TFMA | CY N-allyl | CY N,N diallyl |
| --- | --- | --- | --- | --- | --- | --- |
| Invention 17 | Pd(OAc)$_2$ | heptane | 2h 30 | 23.7 | 5.7 | |
| Invention 18 | Cu$_2$O | heptane | 2h 30 | 39.3 | 54.1 | 11% |

EXAMPLES 19 TO 23

In these examples the influence of various solvents have been studied under the conditions of Example 1. The degree of conversion of trifluoromethylaniline and the yields based on converted N-allylaniline and N,N-diallylaniline are reported below in Table III.

TABLE III

| Test | Catalyst | Influence of the solvent | Time | DC M-TFMA | CY N-allyl | CY N,N-diallyl |
| --- | --- | --- | --- | --- | --- | --- |
| Comparative 5 | — | ∅-O-∅ | 2h 30 | 0.3 | traces | — |
| 19 | Cu | ∅-O-∅ | 2h 30 | 18.4 | 77 | 16 |
| Comparative 6 | — | DMF | 2h 30 | 17.8 | 76.8 | — |
| 20 | Cu | DMF | 2h 30 | 67.6 | 62.9 | 16.7 |
| Comparative 7 | — | toluene | 2h 30 | 1.1 | traces | — |
| 21 | Cu | toluene | 2h 30 | 21.2 | 69.9 | 5.9 |
| Comparative 8 | — | NMP | 2h 30 | 16.9 | 85 | — |
| 22 | Cu | NMP | 2h 30 | 80.4 | 66.7 | 3 |
| Comparative 9 | — | DMF-H$_2$O 2ml-1ml | 2h 30 | 74 | 42 | 9.4 |
| 23 | Cu | DMF-H$_2$O 2 ml-1 ml | 2h 30 | 95.6 | 15.9 | 44.5 |

What is claimed is:

1. A process for the preparation of an N-allylperhaloalkyl-, -perhaloalkoxy- or perhaloalkylthioaniline, which comprises placing a perhaloalkylated, perhaloalkoxylated or perhalothioalkylated aniline and an allyl halide in a solvent medium in contact with an effective amount of a metal catalyst selected from palladium, copper and nickel.

2. A process as claimed in claim 1, wherein the aniline corresponds to the following formula (I):

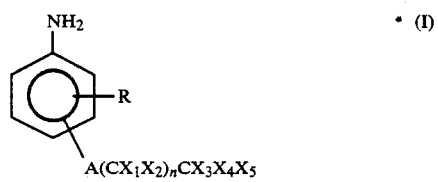

in which
A is a covalent bond or an oxygen or sulfur atom,
$X_1$, $X_2$, $X_3$, $X_4$ and $X_5$ each represent an identical or different halogen atom,
n is equal to 0, 1 or 2, and
R is a hydrogen atom, a halogen atom, an alkyl containing 1 to 4 carbon atoms, an alkoxy containing 1 to 4 carbon atoms or an aryl group.

3. A process as claimed in claim 2, wherein the compound of formula (I) is trifluoromethylaniline.

4. A process as claimed in claim 1, wherein the allyl halide is selected from allyl chloride and bromide.

5. A process as claimed in claim 4, wherein the allyl halide is allyl chloride.

6. A process as claimed in claim 1, wherein the metal catalyst is palladium.

7. A process as claimed in claim 1, wherein the metal catalyst is selected from palladiumdiacetate and dibenzylideneacetonepalladium.

8. A process as claimed in claim 1, wherein the solvent medium is selected from aprotic solvents, ethers, nitriles, halogenated aromatic solvents, halogenated aliphatic solvents and alcohols.

9. A process as claimed in claim 1, wherein the solvent is selected from N-methylpyrrolidone, heptane and acetonitrile.

10. A process as claimed in claim 1, wherein the molar ratio of the allyl halide to the compound of formula (I) is from about 1:1 to 2:1.

11. A process as claimed in claim 3, wherein said trifluoromethylaniline is meta-trifluoromethylaniline and wherein the molar ratio of the allyl halide to meta-trifluoromethylaniline is from about 1:1 to 2:1.

12. A process as claimed in claim 1, wherein the reaction temperature is from about 50° to 120° C.

13. A process as claimed in claim 2, wherein the molar ratio of the metal catalyst to the compound of formula (I) is from about 0.01:1 to 0.5:1.

14. A process as claimed in claim 13, wherein the molar ratio is from about 0.05:1 to 0.2:1.

15. A process as claimed in claim 11, wherein the molar ratio of the catalyst to meta-trifluoromethylaniline is from about 0.01:1 to 0.5:1.

16. A process as claimed in claim 15, wherein the molar ratio of said catalyst to said meta-trifluoromethylaniline is from about 0.05:1 to 0.2:1.

* * * * *